United States Patent [19]
Gante et al.

[11] Patent Number: 5,908,843
[45] Date of Patent: Jun. 1, 1999

[54] PIPERAZINE COMPOUNDS AS FIBRINOGEN INHIBITORS

[75] Inventors: Joachim Gante, Darmstadt; Peter Raddatz; Horst Juraszyk, both of Seeheim; Sabine Bernotat-Danielowski, Bad-Nauheim; Guido Melzer, Hofheim, all of Germany

[73] Assignee: Merck Patent Gesellschaft mit Beschrankter Haftung, Germany

[21] Appl. No.: 08/189,385

[22] Filed: Jan. 31, 1994

[30] Foreign Application Priority Data

Jan. 29, 1993 [DE] Germany .............................. 43 02 485

[51] Int. Cl.[6] ................... A61K 31/495; C07D 295/155; C07D 241/08; C07D 403/12
[52] U.S. Cl. ......................... 514/255; 514/252; 514/253; 544/357; 544/370; 544/373; 544/384; 544/390; 544/391; 544/399; 544/400
[58] Field of Search ..................... 544/357, 370, 544/373, 384, 390, 391, 399, 400; 514/252, 253, 255

[56] References Cited

U.S. PATENT DOCUMENTS

| | | | |
|---|---|---|---|
| 5,084,466 | 1/1992 | Alig et al. ................................ | 514/353 |
| 5,294,616 | 3/1994 | Duggan et al. ......................... | 544/398 |
| 5,294,713 | 3/1994 | Sugihara et al. ....................... | 544/384 |

FOREIGN PATENT DOCUMENTS 0 462 960   12/1991   European Pat. Off. .

OTHER PUBLICATIONS

Born, Nature, vol. 194, No. 4832, pp. 927–929 (Jun. 9, 1962).
Roux et al., The Journal of Pharmacology and Experimental Therapeutics, vol. 264, No. 1, pp. 501–508 (1993).
Müller et al in *Receptor Data for Biological Experiments* (Doods & van Meel, Editors), Chapter 20, pp. 112–117 (1991).

*Primary Examiner*—Emily Bernhardt
*Attorney, Agent, or Firm*—Millen, White, Zelano, & Branigan, P.C.

[57] ABSTRACT

Novel piperazine derivatives of formula I:

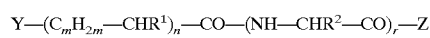

wherein

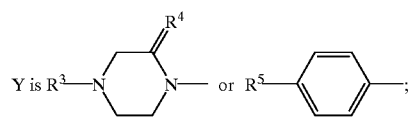

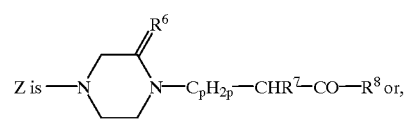

if Y is $R^3$

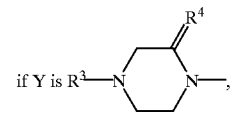

Z can also be

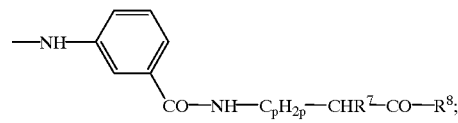

$R^1$, $R^2$ and $R^7$ are each, independently, $-C_tH_{2t}-R^9$, benzyl, hydroxybenzyl, imidazolylmethyl or indolylmethyl;
$R^3$ is H or $H_2N-C(=NH)-$;
$R^4$ and $R^6$ are each, independently, (H,H) or $=O$;
$R^5$ is H, $H_2N-C(=NH)-$ or $H_2N-C(=NH)-NH$;
$R^8$ is OH, OA or NHOH;
$R^9$ is H, OH, $NH_2$, SH, SA, COOH, $CONH_2$ or $NH-C(=NH)-NH_2$;
A is in each case, independently, alkyl having 1–4 C atoms;
m and t are each, independently, 0, 1, 2, 3 or 4;
n and r are each, independently, 0 or 1; and
p is 0, 1 or 2,
inhibit the binding of fibrinogen to the fibrinogen receptor and can be used for the treatment of thrombosis, apoplexy, cardiac infarctus, inflammation, arteriosclerosis and tumors.

27 Claims, No Drawings

PIPERAZINE COMPOUNDS AS FIBRINOGEN INHIBITORS

SUMMARY OF THE INVENTION

The invention relates to novel compounds of formula I:

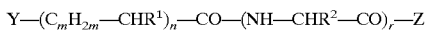

wherein

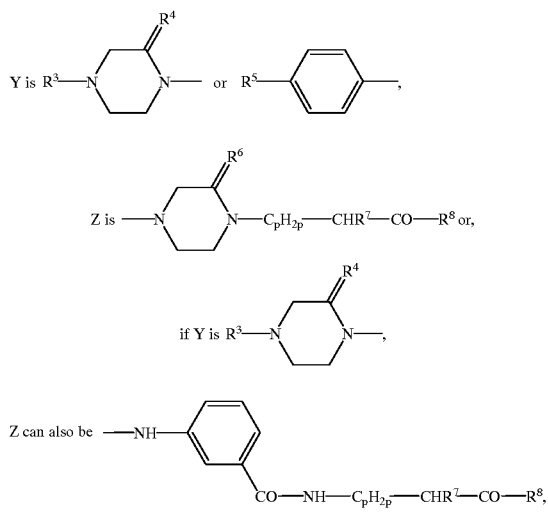

$R^1$, $R^2$ and $R^7$ are each $-C_tH_{2t}-R^9$, benzyl, hydroxybenzyl, imidazolylmethyl or indolylmethyl, $R^3$ is H or $H_2N-C(=NH)-$, $R^4$ and $R^6$ are each (H,H) or =O, $R^5$ is H, $H_2N-C(=NH)-$ or $H_2N-C(=NH)-NH-$, $R^8$ is OH, OA or NHOH, $R^9$ is H, OH, $NH_2$, SH, SA, COOH, $CONH_2$ or $NH-C(=NH)-NH_2$, A is in each case alkyl having 1–4 C atoms, m and t are each 0, 1, 2, 3 or 4, n and r are each 0 or 1 and p is 0, 1 or 2, and wherein the piperazine rings can be substituted by 1 to 4 groups A, and their salts.

Similar compounds are known from EP-A1-0 381 033 and U.S. Pat. No. 5,084,466.

An object of the invention is to provide novel compounds with valuable properties, especially those which can be used for the preparation of drugs.

Upon further study of the specification and appended claims, further objects and advantages of this invention will become apparent to those skilled in the art.

These objects have been achieved by the compounds according to the invention. It has been found that the compounds of formula I and their solvates and salts possess valuable pharmacological properties coupled with a good tolerance. In particular, they inhibit the binding of fibrinogen, fibronectin and the von Willebrand factor to the fibrinogen receptor of blood platelets (glycoprotein IIb/IIa) as well as the binding of the latter and of other adhesive proteins, such as vitronectin, collagen and laminin, to the corresponding receptors on the surface of various cell types.

The compounds thus influence cell—cell and cell-matrix interactions. In particular, they prevent the formation of blood platelet thrombi and can therefore be used for the treatment of thrombosis, apoplexy, cardiac infarctus, inflammation and arteriosclerosis. The compounds also have an effect on tumor cells by inhibiting them from forming metastases. Thus they can also be used as anti-tumoral agents.

There is evidence that tumor cells spreading from a solid tumor into the vasculature are carried by microthrombi and thus are protected from being detected by cells of the immune system. The second step of attachment to the vessel wall seems to be facilitated by microthrombi as well. Since the formation of thrombi is mediated by fibrinogen binding to the fibrinogen receptor glycoprotein IIb/IIIa on activated platelets, fibrinogen binding inhibitors can be expected to be effective as antimetastatics. This is applicable to all tumors.

Also, since fibrinogen binding inhibitors are ligands for the fibrinogen receptor on platelets, they can be used as diagnostic tools for detection and localization of thrombi in the vasculature in vivo.

Thus, for example, in accordance with known procedures, the fibrinogen binding inhibitors can be labelled with a signal generating or detectable moiety whereby, once the labelled fibrinogen binding inhibitor is bound to a fibrinogen receptor on platelets, it is possible to detect and locate thrombi.

Fibrinogen binding inhibitors are also very effective as research tools for studying the metabolism of platelets and the different activation states or intracellular signalling mechanisms of the fibrinogen receptor.

For example, as described above, the fibrinogen binding inhibitor can be labelled with a signal generating or detectable moiety. The fibrinogen binding inhibitor-signal generating/detectable moiety conjugate can then be employed in vitro as a research tool. By binding the conjugate to fibrinogen receptors, it is possible to monitor and study the metabolism of platelets, as well as the activation states and signalling mechanisms of the fibrinogen receptors.

The properties of the compounds can be demonstrated by methods described in EP-A1-0 462 960. The inhibition of the binding of fibrinogen to the fibrinogen receptor can be demonstrated by the method indicated in EP-A1-0 381 033 and U.S. Pat. No. 5,084,466. The thrombocyte aggregation inhibiting action can be demonstrated in vitro by the method of Born (Nature 4832, 927–929, 1962).

The invention further relates to a process for the preparation of a compound of formula I given above, and its salts, characterized in that (a) a compound of formula I is freed from one of its functional derivatives by treatment with a solvolyzing or hydrogenolyzing agent, or (b) a carboxylic acid of formula II:

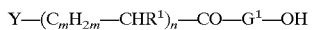

wherein $G^1$ (a) is absent, (b) is —NH—CHR$^2$—CO— or (c) is 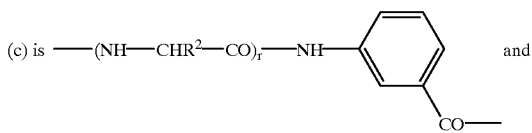

Y, R$^1$, R$^2$, m, n and r are defined as indicated above, or one of its reactive derivatives,
is reacted with an amino compound of formula III:

H—G$^2$     III wherein
G$^2$ (a) is —(NH—CHR$^2$—CO)$_r$—Z,
(b) is Z or
(c) is —NH—C$_p$H$_{2p}$—CHR$^7$—CO—R$^8$ and
Z, R$^2$, R$^7$, R$^8$, r and p are defined as indicated above, or (c) to prepare a compound of formula I wherein R$^3$ or R$^5$ is H$_2$N—C(=NH)—, ammonia is added on to a nitrile which has formula I except that it contains a CN group in place of the radical R$^3$ or R$^5$, and/or, if appropriate, a carboxylic acid of formula I (R$^8$=OH) is converted to a corresponding ester (I, R$^8$=OA) or to the corresponding hydroxamic acid (I, R$^8$=NHOH), and/or an H atom is replaced with an amidino group by treatment with an amidine-forming agent, or an ester of formula I (R$^8$=OA) is saponified, and/or a compound of formula I is converted to one of its salts by treatment with an acid or a base.

Some of the compounds of formula I possess chiral centers and can therefore occur in several enantiomeric forms. All these forms (for example D and L forms) and mixtures thereof (for example the DL forms) are included in formula I.

Above and below, the radicals or parameters Y, Z, R$^1$ to R$^9$, A, G$^1$, G$^2$, m, n, p, r and t are defined as indicated for formulae I, II or III, unless expressly indicated otherwise.

The groups A are in each case alkyl groups having 1–4, preferably 1 or 2 C atoms, especially methyl or ethyl, or else propyl, isopropyl, butyl, isobutyl, sec-butyl or tert-butyl. If several groups A are present in the compound of formula I, they can be identical to or different from one another.

The parameter m is preferably 0 or 1; t is preferably 0, or else 1, 2, 3, or 4; n is preferably 1, or else 0; r is preferably 0, or else 1; p is preferably 1, or else 0 or 2.

The groups —NH—CHR$^2$—CO— and —NH—C$_p$H$_{2p}$—CHR$^7$—CO— can be in particular the radicals of naturally occurring amino acids, preferably —NH—CH$_2$—CO— (glycine radical), or else the radicals of L- or D-alanine, L- or D-valine, L- or D-leucine, L- or D-isoleucine, L- or D-phenylalanine, L- or D-tyrosine, L- or D-histidine, L- or D-tryptophan, L- or D-serine, L- or D-threonine, L- or D-ornithine, L- or D-lysine, L- or D-cysteine, L- or D-methionine, L- or D-aspartic acid, L- or D-asparagine and L- or D-arginine. The group —NH—C$_p$H$_{2p}$—CHR$^7$—CO— is preferably also —NH—CH$_2$CH$_2$—CO— (β-alanine radical) or —NH—(CH$_2$)$_3$—CO— (4-aminobutyric acid radical).

R$^1$, R$^2$, R$^7$ and R$^9$ are each preferably H. R$^3$ is preferably H$_2$N—C(=NH)— (amidino). R$^4$ and R$^6$ are each preferably (H,H). R$^5$ is preferably H$_2$N—C(=NH)—NH— (guanidino). R$^8$ is preferably OH, or else preferably OA, especially OCH$_3$ or OC$_2$H$_5$.

Accordingly the group —(C$_m$H$_{2m}$—CHR$^1$)$_n$—CO—(NH—CHR$^2$CO)$_r$— is preferably —CO—, —CH$_2$—CO—, —CO—NH—CH$_2$—CO— or —CH$_2$CH$_2$—CO—.

The piperazine rings can additionally be substituted by 1–4 groups A, preferably by 1–4 methyl groups. Preferred substituted piperazine rings are 2-methylpiperazine-1,4-diyl, 2,5-dimethylpiperazine-1,4-diyl, 2,6-dimethylpiperazine-1,4-diyl and 2,3,5,6-tetramethylpiperazine-1,4-diyl.

Preferred compounds of formula I are those in which at least one of the indicated radicals, groups and/or parameters has one of the preferred meanings given. Some groups of preferred compounds are those of formulae Ia to Ig, which correspond to formula I and wherein the unspecified radicals and/or parameters are defined as indicated for formula I, but wherein in Ia Y is 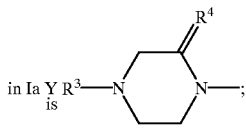

in Ib Y is 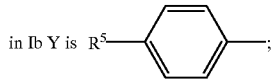

in Ic Y is 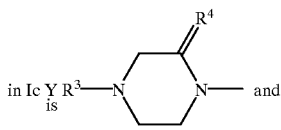 and

Z is 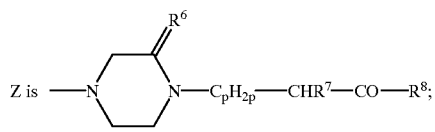

in Id Y is 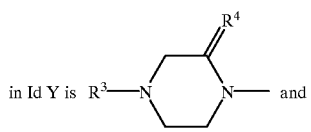 and

Z is—NH— 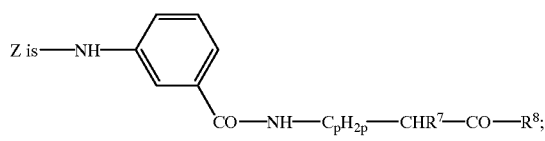

in Ie Y is 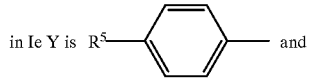 and

Z is 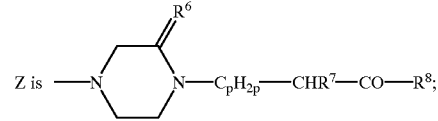

in If YH$_2$N—C(=NH)— 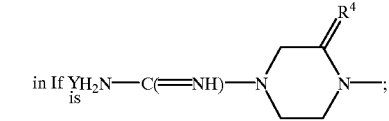

-continued in Ig Y is H$_2$N—C(═NH)—NH—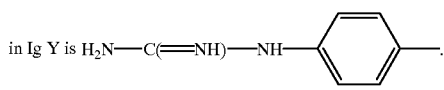

Other preferred compounds are those of formulae Ih and Iah to Igh, which correspond to formulae I and Ia to Ig, but wherein the group —(C$_m$H$_{2m}$—CHR$^1$)$_n$—CO—(NH—CHR$^2$—CO)$_r$— is additionally —CO—, —CH$_2$—CO—, —CO—NH—CH$_2$—CO— or —CH$_2$CH$_2$CO—.

Other preferred compounds are those of formulae Ii, Iai to Ihi and Iahi to Ighi, which correspond to formulae I, Ia to Ih and Iah to Igh, but wherein the group —C$_p$H$_{2p}$—CHR$^7$—CO—R$^8$ is additionally —CH$_2$COOH, —CH$_2$CH$_2$COOH, —(CH$_2$)$_3$—COOR, —CH(COOH)—CH$_2$COOH, —CH$_2$COOA, —CH$_2$CH$_2$COOA, —(CH$_2$)$_3$—COOA or —CH(COOA)—CH$_2$COOA.

The compounds of formula I and also the starting materials for their preparation are prepared by methods known per se, such as those described in the literature (for example in the standard works like Houben-Weyl, Methoden der organischen Chemie (Methods of Organic Chemistry), Georg-Thieme-Verlag, Stuttgart; also EP-A1-0381033 and EP-A1-0462960), under reaction conditions which are known and appropriate for said reactions. It is also possible here to make use of variants known per se, which are not mentioned in greater detail in the present description.

If desired, the starting materials can also be formed in situ so that they are immediately reacted further to give the compounds of formula I rather than being isolated from the reaction mixture.

The compounds of formula I can be obtained by being freed from their functional derivatives by solvolysis, especially hydrolysis, or by hydrogenolysis.

Preferred starting materials for solvolysis or hydrogenolysis are those which have formula I except that they contain appropriate protected amino and/or hydroxy groups in place of one or more free amino and/or hydroxy groups, preferably those carrying an amino-protecting group in place of an H atom bonded to an N atom, and especially those carrying an R'—NH group in place of an H$_2$N group, R' being an amino-protecting group, and/or those carrying a hydroxy-protecting group in place of the H atom of a hydroxy group, for example those which have formula I except that they carry a group —C$_r$H$_{2r}$—OR" in place of a group —C$_r$H$_{2r}$—R$^9$, and/or a group —OR" in place of a group R$^8$, R" being a hydroxy-protecting group.

There may also be several—identical or different—protected amino and/or hydroxy groups in the molecule of the starting material. If the protecting groups present are different from one another, they can be cleaved selectively in many cases.

The expression "amino-protecting group" is generally known and refers to groups which are suitable for protecting an amino group from chemical reactions (blocking an amino group), but which can easily be removed after the desired chemical reaction has been carried out at another site of the molecule. Typical examples of such groups are especially unsubstituted or substituted acyl, aryl (for example 2,4-dinitrophenyl (DNP)), aralkoxymethyl (for example benzyloxymethyl (BOM)) or aralkyl (for example benzyl, 4-nitrobenzyl, triphenylmethyl) groups. As the amino-protecting groups are removed after the desired reaction (or reaction sequence), their nature and size are not critical, although those having 1–20, especially 1–8 C atoms are preferred. The expression "acyl group" is to be understood in the broadest sense in connection with the present process. It includes acyl groups derived from aliphatic, araliphatic, aromatic or heterocyclic carboxylic acids or sulfonic acids, especially alkoxycarbonyl, aryloxycarbonyl and, in particular, aralkoxycarbonyl groups. Examples of such acyl groups are alkanoyl such as acetyl, propionyl and butyryl; aralkanoyl such as phenylacetyl; aroyl such as benzoyl or toluyl; aryloxyalkanoyl such as phenoxyacetyl; alkoxycarbonyl such as methoxycarbonyl, ethoxycarbonyl, 2,2,2-trichloroethoxycarbonyl, isopropoxycarbonyl, tert-butoxycarbonyl (BOC) or 2-iodoethoxycarbonyl; and aralkoxycarbonyl such as benzyloxycarbonyl (CBZ), 4-methoxybenzyloxycarbonyl or 9-fluorenylmethoxycarbonyl (FMOC). Preferred amino-protecting groups are BOC, DNP and BOM, as well as CBZ, benzyl and acetyl.

The expression "hydroxy-protecting group" is also generally known and refers to groups which are suitable for protecting a hydroxy group from chemical reactions, but which can easily be removed after the desired chemical reaction has been carried out at another site of the molecule. Typical examples of such groups are the above-mentioned unsubstituted or substituted aryl, aralkyl or acyl groups, as well as alkyl groups. The nature and size of the hydroxy-protecting groups is not critical as they are removed after the desired chemical reaction or reaction sequence; preferred groups are those having 1–20, especially 1–10 C atoms. Examples of hydroxy-protecting groups are, inter alia, tert-butyl, benzyl, p-nitrobenzoyl, p-toluenesulfonyl and acetyl, benzyl and acetyl being particularly preferred.

The functional derivatives of the compounds of formula I to be used as starting materials can be prepared by conventional methods of amino acid and peptide synthesis, such as those described for example in the cited standard works and patent applications, for example also by Merrifield's solid phase method.

The freeing of the compounds of formula I from their functional derivatives is effected—depending on the protecting group used—for example with strong acids, conveniently with trifluoroacetic acid or perchloric acid, or else with other strong inorganic acids such as hydrochloric acid or sulfuric acid, strong organic carboxylic acids such as trichloroacetic acid, or sulfonic acids such as benzene- or p-toluene-sulfonic acid. The presence of an additional inert solvent is possible, but not always necessary.

Suitable inert solvents are preferably organic, for example carboxylic acids such as acetic acid, ethers such as tetrahydrofuran or dioxane, amides such as dimethylformamide (DMF), and halogenated hydrocarbons such as dichloromethane, or else alcohols such as methanol, ethanol or isopropanol, and water. Mixtures of the above-mentioned solvents are also suitable. Trifluoroacetic acid is preferably used in excess without the addition of another solvent; perchloric acid is preferably used in the form of a mixture of acetic acid and 70% perchloric acid in a ratio of 9:1. The reaction temperatures for the cleavage are conveniently about 0–50°; the operating temperature is preferably 15–30° (room temperature).

The BOC group can preferably be cleaved for example with 40% trifluoroacetic acid in dichloromethane or with about 3 to 5 N HCl in dioxane at preferably 15–60° and the FMOC group can preferably be cleaved for example with an approximately 5–20% solution of dimethylamine, diethylamine or piperidine in DMF at preferably 15–50°. The DNP group is also cleaved for example with an approximately 3–10% solution of 2-mercaptoethanol in DMF/water at preferably 15–30°.

Protecting groups which can be removed by hydrogenolysis (for example BOM, CBZ or benzyl) can be cleaved for example by treatment with hydrogen in the presence of a catalyst (for example a noble metal catalyst such as palladium, conveniently on a support such as charcoal). Solvents which are suitable for this purpose are those indicated above, for example especially alcohols such as methanol or ethanol, or amides such as DMF. As a rule, the hydrogenolysis is carried out at temperatures of preferably about 0–100° and pressures of preferably 1–200 bar, particularly at 20–30° and 1–10 bar. Hydrogenolysis of the CBZ group is successful for example on 5–10% Pd/C in methanol at preferably 20–30°.

Compounds of formula I can also be obtained by direct condensation from a carboxylic acid component (formula II) and an amino component (formula III). Examples of suitable carboxylic acid components are those of the partial formulae (a) Y—$(C_mH_{2m}$—$CHR^1)_n$—COOH, (b) Y—$(C_mH_{2m}$—$CHR^1)_n$—CO—NH—$CHR^2$—COOH or

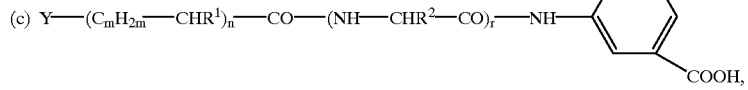

(c) Y—$(C_mH_{2m}$—$CHR^1)_n$—CO—(NH—$CHR^2$—CO)$_r$—NH—⟨ ⟩—COOH, and examples of suitable amino components are those of the partial formulae (a) H—(NH—$CHR^2$—CO)$_r$—Z, (b) H—Z or (c) $H_2N$—$C_pH_{2p}$—$CHR^7$—CO—$R^8$.

Said condensation reaction is conveniently carried out by conventional methods of peptide synthesis, such as those described for example in Houben-Weyl, loc. cit., volume 15/II, pages 1–806 (1974).

The reaction is preferably performed in the presence of a dehydrating agent, for example a carbodiimide such as dicyclohexylcarbodiimide (DCCI) or N-dimethylaminopropyl-N'-ethylcarbodiimide (DAPECI), or else propanephosphonic anhydride (compare Angew. Chem. 92, 129 (1980)), diphenylphosphorylazide or 2-ethoxy-N-ethoxycarbonyl-1,2-dihydroquinoline, in an inert solvent, for example a halogenated hydrocarbon such as dichloromethane, an ether such as TEF or dioxane, an amide such as DMF or dimethylacetamide, or a nitrile such as acetonitrile, at temperatures of preferably about –10–40, particularly 0–30°.

In the reaction, II or III can also be replaced with suitable reactive derivatives of these substances, for example those in which reactive groups are blocked with protecting groups as an intermediate measure. The acid derivatives II can be used for example in the form of their activated esters, which are conveniently formed in situ, for example by the addition of HOBt or N-hydroxysuccinimide.

An amidine of formula I ($R^3$ or $R^5$=$H_2N$—C(=NH)—) can also be prepared by adding ammonia on to a nitrile which has formula I except that it contains a CN group in place of $R^3$ or $R^5$. The addition reaction is preferably effected in several steps, in a manner known per se, as follows: a) the nitrile is converted with $H_2S$ to a thioamide, which is converted with an alkylating agent, for example $CH_3I$, to the corresponding S-alkylimidothioester, which in turn reacts with $NH_3$ to give the amidine, b) the nitrile is converted with an alcohol, for example ethanol, in the presence of HCl, to the corresponding imidoester, which is treated with ammonia, or c) the nitrile is reacted with lithium bis(trimethylsilyl)amide and the product is then hydrolysed.

Some of the starting materials for the indicated process variants, for example. Those of formulae II and III, are known. Those which are not known can be prepared by known methods, for example the abovementioned methods involving condensation and the cleavage of protecting groups.

If desired, a carboxylic acid group in a compound of formula I can be esterified or converted to a hydroxamic acid group, or an ester group can be saponified.

For esterification, an acid of formula I ($R^8$=OH) can be treated with an excess of an alcohol of the formula R—OH, conveniently in the presence of a strong acid such as hydrochloric acid or sulfuric acid, at temperatures of preferably 0–100, particularly 20–50°.

To prepare hydroxamic acids of formula I ($R^8$=NHOH), a corresponding ester of formula I ($R^8$=OA). is conveniently treated with hydroxylamine, which can be freed from one of its salts, for example the hydrochloride, with an-alkali metal alcoholate, for example sodium ethylate. The reaction is conveniently carried out in the presence of an inert solvent, for example an alcohol such as methanol, ethanol or isopropanol, at temperatures of preferably about 0–40, particularly 15–30°.

Furthermore, a compound of formula I wherein $R^8$ is OA can conveniently be converted to the corresponding compound of formula I wherein $R^8$ is OH by selective solvolysis using one of the methods indicated above, for example with NaOH or KOH in water/dioxane at temperatures of preferably 0–40°, particularly 10–30°.

Furthermore, an H atom in a compound of formula I can be replaced with an amidino group by treatment with an amidine-forming agent. Suitable starting materials are preferably piperazine derivatives wherein $R^3$=H; the preferred amidine-forming agent is 1-amidino-3,5-dimethylpyrazole, which is used especially in the form of its nitrate. The reaction is conveniently carried out with the addition of a base such as triethylamine or ethyldiisopropylamine, in an inert solvent or solvent mixture, for example water/dioxane, at temperatures of preferably 0–120°, particularly 60–120°.

A base of formula I can be converted with an acid to the corresponding acid addition salt. Acids which are particularly suitable for this reaction are those yielding physiologically acceptable salts. Thus it is possible to use inorganic acids, for example sulfuric acid, nitric acid, hydrohalic acids such as hydrochloric acid or hydrobromic acid, phosphorus acids such as orthophosphoric acid, and sulfamic acid, as well as organic acids, especially aliphatic, alicyclic, araliphatic, aromatic or heterocyclic monobasic or polybasic carboxylic, sulfonic or sulfuric acids, for example formic acid, acetic acid, trifluoroacetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalenemonosulfonic and naphthalenedisulfonic acids and laurylsulfuric acid. Salts with physiologically unacceptable acids, for example picrates, can be used to isolate and/or purify the compounds of formula I.

The novel compounds of formula I and their physiologically acceptable salts can be used for the manufacture of pharmaceutical preparations by being converted to a suitable dosage form together with at least one excipient or adjunct and, if desired, together with one or more other active ingredients. The resulting preparations can be used as drugs in human or veterinary medicine. Possible excipients are organic or inorganic substances which are suitable for enteral (for example oral or rectal) or parenteral administration or for administration in the form of an inhalation spray, and which do not react with the novel compounds, for example water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Tablets, coated tablets, capsules, syrups, juices or drops, in particular, are used for oral administration; film-coated tablets and capsules with coatings or shells resistant to gastric juices are of special value. Suppositories are used for rectal administration and solutions, preferably oily or aqueous solutions, as well as suspensions, emulsions or implants, are used for parenteral administration.

For administration as an inhalation spray, it is possible to use sprays which contain the active ingredient either dissolved or suspended in a propellant gas mixture. It is convenient here to use the active ingredient in micronized form, it being possible for one or more additional physiologically compatible solvents, for example ethanol, to be present. Inhalation solutions can be administered with the aid of conventional inhalers. The novel compounds can also be lyophilized and the resulting lyophilizates used for example for the manufacture of injection preparations. Said preparations can be sterilized and/or can contain adjuncts such as preservatives, stabilizers and/or wetting agents, emulsifiers, salts for influencing the osmotic pressure, buffer substances, colors and/or flavorings. If desired, they can also contain one or more other active ingredients, for example one or more vitamins.

As a rule, the substances according to the invention are administered analogously to other known and commercially available peptides, but in particular analogously to the compounds described in EP-A-249096, preferably in dosages of about 5 mg–1 g, especially 50–500 mg per dosage unit. The daily dosage is preferably about 0.1–20 mg/kg, especially 1–10 mg/kg of body weight. However, the particular dose for each individual patient depends on a very wide variety of factors, for example the efficacy of the particular compound used, age, body weight, general state of health, sex, diet, time and route of administration, rate of excretion, drug combination and severity of the particular disease for which the therapy is intended. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, unless otherwise indicated, all parts and percentages are by weight.

The entire disclosure of all applications, patents and publications, cited above and below, and of corresponding German application P 43 02 485.8 are hereby incorporated by reference.

EXAMPLES

Above and below, all temperatures are given in ° C. In the Examples which follow, "conventional working-up" means: Water is added where necessary, the pH is adjusted to values between 2 and 8, depending on the constitution of the end product, extraction is carried out with ethyl acetate or dichloromethane, the organic phase is separated off, dried over sodium sulfate and evaporated and the residue is purified by chromatography on silica gel and/or by crystallization. FAB=($M^+$+1) peak in the mass spectrum, obtained by the Fast Atom Bombardment method.

Example 1

A mixture of 10 g of ethyl 3-(4-(4-(3-BOC-guanidino) benzoyl)-2-oxopiperazin-1-yl)propionate (m.p. 143°; FAB 462; obtainable by condensing 4-(3-BOC-guanidino) benzoic acid with ethyl 3-(2-oxopiperazin-1-yl)propionate), 400 ml of dioxane and 56 ml of 1 N aqueous NaOH solution is stirred for 5 hours at 20°. It is evaporated, the residue is dissolved in water, the solution is washed several times with ethyl acetate, and HCl is added to pH 4. Extraction is carried out with ethyl acetate, the extract is dried and evaporated, the resulting crude 3-(4-(4-(3-BOC-guanidino)benzoyl)-2-oxopiperazin-1-yl)propionic acid is dissolved in 200 ml of 4 N HCl in dioxane and the solution is stirred for 3 hours at 20° and worked up in conventional manner to give 3-(4-(4-guanidinobenzoyl)-2-oxopiperazin-1-yl)propionic acid, m.p. 110° (decomposition).

4-(4-Guanidinobenzoyl)-2-oxopiperazin-1-ylacetic acid, m.p. 98° (decomposition), is obtained analogously from ethyl 4-(4-(3-BOC-guanidino) benzoyl)-2-oxopiperazin-1-ylacetate (oil; FAB 448; obtainable by condensing 4-(3-BOC-guanidino)benzoic acid with ethyl 2-oxopiperazin-1-ylacetate) by saponification and subsequent cleavage of the BOC group.

4-(4-Amidinobenzamidoacetyl)piperazin-1-ylacetic acid, FAB 348, is obtained analogously from 4-(4-BOC-amidinobenzamidoacetyl)piperazin-1-ylacetic acid (FAB 448; obtainable by condensing 4-BOC-amidinobenzamidoacetic acid with benzyl piperazin-1-ylacetate to give benzyl 4-(4-BOC-amidinobenzamidoacetyl)piperazin-1-ylacetate and hydrogenolyzing the benzyl ester group).

Example 2

A solution of 1 g of benzyl 4-(4-(4-(3-CBZ-guanidino) benzoyl)piperazin-1-yl)butyrate (FAB 558; obtainable by condensing 4-(3-CBZ-guanidino)benzoic acid with benzyl 4-(piperazin-1-yl)butyrate) in a mixture of 38 ml of methanol, 6 ml of water and 6 ml of acetic acid is hydrogenated on 0.6 g of 5% Pd/C at 20° and 1 bar until the uptake of $H_2$ has ceased. It is filtered, the filtrate is evaporated and the residue is recrystallized from ethyl acetate to give 4-(4-(4-guanidinobenzoyl)piperazin-1-yl)butyric acid, FAB 334.

The following are obtained analogously by hydrogenolysis:

3-(3-(4-amidinopiperazin-1-ylacetamido)benzamido) propionic acid, m.p. 270° (decomposition), from benzyl 3-(3-(4-CBZ-amidinopiperazin-1-ylacetamido) benzamido)propionate (FAB 601; obtainable by reacting tert-butyl piperazin-1-ylacetate with N-CBZ-S-methylisothiourea to give tert-butyl 4-CBZ-amidinopiperazin-1-ylacetate, cleaving the tert-butyl group with 4 N HCl in dioxane and condensing the resulting 4-CBZ-amidinopiperazin-1-ylacetic acid with benzyl 3-(3-aminobenzamido)propionate);

4-(4-guanidinobenzamidoacetyl)piperazin-1-ylacetic acid, hydrochloride m.p. 124° (decomposition), from benzyl 4-(4-guanidinobenzamidoacetyl)piperazin-1-ylacetate (m.p. 248°; obtainable by condensing 4-guanidinobenzoic acid with benzyl 4-aminoacetylpiperazin-1-ylacetate);

3-(3-(piperazin-1-ylcarboxamidoacetamido)benzamido) propionic acid, m.p. 1230, from benzyl 3-(3-(4-CBZ-piperazin-1-ylcarboxamidoacetamido)benzamido) propionate (FAB 602; obtainable by reacting 1-CBZ-piperazine with benzyl 3-(3-(isocyanatoacetamido) benzamido)propionate);

3-(3-(4-amidinopiperazin-1-ylcarboxamidoacetamido) benzamido)propionic acid, hydrochloride FAB 420, from benzyl 3-(3-(4-CBZ-amidinopiperazin-1-ylcarboxamidoacetamido)benzamido)propionate (FAB 664; obtainable by reacting 1-CBZ-amidinopiperazine with benzyl 3-(3-isocyanatoacetamidobenzamido) propionate);

4-(4-amidinopiperazin-1-ylacetyl)piperazin-1-ylacetic acid, m.p. 272° (decomposition), from benzyl 4-(4-CBZ-amidinopiperazin-1-ylacetyl)piperazin-1-ylacetate (Rf 0.44 (dichloromethane/methanol 9:1); obtainable by condensing 4-CBZ-amidinopiperazin-1-ylacetic acid with benzyl piperazin-1-ylacetate);

3-(3-(2-oxopiperazin-1-ylacetamido)benzamido) propionic acid, m.p. 225°, from benzyl 3-(3-(4-CBZ-2-oxopiperazin-1-ylacetamido)benzamido)propionate (FAB 573; obtainable by condensing 4-CBZ-2-oxopiperazin-1-ylacetic acid with benzyl 3-(3-aminobenzamido)propionate);

3-(2-oxopiperazin-1-ylacetamido)benzamidoacetic acid, m.p. 167°, from benzyl 3-(4-CBZ-2-oxopiperazin-1-ylacetamido)benzamidoacetate (FAB 559; obtainable from 3-(4-CBZ-2-oxopiperazin-1-ylacetamido)benzoic acid and benzyl glycinate);

3-(4-amidino-2-oxopiperazin-1-ylacetamido) benzamidoacetic acid, m.p. >300°, from benzyl 3-(4-CBZ-amidino-2-oxopiperazin-1-ylacetamido) benzamidoacetate (FAB 601; obtainable by condensing 3-(4-CBZ-amidino-2-oxopiperazin-1-ylacetamido) benzoic acid with benzyl glycinate);

3-(3-(2-oxopiperazin-1-ylacetamido)benzamido) propionic acid, FAB 349, from benzyl 3-(3-(4-CBZ-2-oxopiperazin-1-ylacetamido)benzamido)propionate (FAB 573; obtainable from 3-(4-CBZ-2-oxopiperazin-1-ylacetamido)benzoic acid and benzyl β-alaninate);

3-(3-(4-amidino-2-oxopiperazin-1-ylacetamido) benzamido)propionic acid, m.p. 283° (decomposition), from benzyl 3-(3-(4-CBZ-amidino-2-oxopiperazin-1-ylacetamido)benzamido)propionate (FAB 615; obtainable by condensing 3-(4-CBZ-amidino-2-oxopiperazin-1-ylacetamido)benzoic acid with benzyl β-alaninate);

4-(piperazin-1-ylcarboxamidoacetyl)piperazin-1-ylacetic acid, m.p. 150° (decomposition), from benzyl 4-(4-CBZ-piperazin-1-ylcarboxamidoacetyl)piperazin-1-ylacetate (FAB 538; obtainable by condensing 4-CBZ-piperazin-1-ylcarboxamidoacetic acid with benzyl piperazin-1-ylacetate);

4-(4-amidinopiperazin-1-ylcarboxamidoacetyl)piperazin-1-ylacetic acid, m.p. 190–195° (decomposition), from benzyl 4-(4-CBZ-amidinopiperazin-1-ylcarboxamidoacetyl)piperazin-1-ylacetate (FAB 580; obtainable by condensing 4-CBZ-amidinopiperazin-1-ylcarboxamidoacetic acid with benzyl piperazin-1-ylacetate);

4-(4-guanidinobenzoyl)-2-oxopiperazin-1-ylacetic acid, m.p. 98° (decomposition), from benzyl 4-(4-(3-CBZ-guanidino)benzoyl)-2-oxopiperazin-1-ylacetate (FAB 544; obtainable by condensing 4-(3-CBZ-guanidino) benzoic acid with benzyl 2-oxopiperazin-1-ylacetate);

3-(piperazin-1-ylcarboxamidoacetamido) benzamidoacetic acid, m.p. 188°, from benzyl 3-(4-CBZ-piperazin-1-ylcarboxamidoacetamido) benzamidoacetate (FAB 588; obtainable from 3-(4-CBZ-piperazin-1-ylcarboxamidoacetamido)benzoic acid and benzyl glycinate);

3-(4-amidinopiperazin-1-ylcarboxamidoacetamido) benzamidoacetic acid, m.p. 234°, from benzyl 3-(4-CBZ-amidinopiperazin-1-ylcarboxamidoacetamido) benzamido acetate (FAB 630; obtainable by condensing 4-CBZ-amidinopiperazin-1-ylcarboxamidoacetic acid with benzyl 3-aminobenzamidoacetate);

3-(4-amidinopiperazin-1-ylacetamido)benzamidoacetic acid, m.p. 180–185° (decomposition), from benzyl 3-(4-CBZ-amidinopiperazin-1-ylacetamido) benzamidoacetate (FAB 587; obtainable by condensing 3-(4-CBZ-amidinopiperazin-1-ylacetamido)benzoic acid with benzyl glycinate);

4-(4-(4-amidinopiperazin-1-ylacetyl)piperazin-1-yl) butyric acid, m.p. 253° (decomposition), from benzyl 4-(4-(4-CBZ-amidinopiperazin-1-ylacetyl)piperazin-1-yl)butyrate (FAB 565; obtainable by condensing 4-CBZ-amidinopiperazin-1-ylacetic acid (m.p. 124°) with benzyl 4-(piperazin-1-yl)butyrate);

3-(4-(4-guanidinobenzoyl)-2-oxopiperazin-1-yl) propionic acid, m.p. 110° (decomposition), from benzyl 3-(4-(4-(3-CBZ-guanidino)benzoyl)-2-oxopiperazin-1-yl)propionate (FAB 558; obtainable by condensing 4-(3-CBZ-guanidino)benzoic acid with benzyl 3-(2-oxopiperazin-1-yl)propionate);

3-(3-(piperazin-1-ylcarboxamido)benzamido)propionic acid, FAB 321, from benzyl 3-(3-(4-CBZ-piperazin-1-ylcarboxamido)benzamido)propionate (FAB 545; obtainable by condensing 3-(4-CBZ-piperazin-1-ylcarboxamido)benzoic acid and benzyl β-alaninate);

3-(3-(4-amidinopiperazin-1-ylcarboxamido)benzamido) propionic acid, m.p. 234° (decomposition), from benzyl 3-(3-(4-CBZ-amidinopiperazin-1-ylcarboxamido) benzamido)propionate (FAB 587; obtainable by condensing 3-(4-CBZ-amidinopiperazin-1-ylcarboxamido)benzoic acid with benzyl β-alaninate);

3-(piperazin-1-ylcarboxamido)benzamidoacetic acid, FAB 307, from benzyl 3-(4-CBZ-piperazin-1-ylcarboxamido)benzamidoacetate (FAB 531; obtainable by condensing 3-(4-CBZ-piperazin-1-ylcarboxamido)benzoic acid with benzyl glycinate);

3-(4-amidinopiperazin-1-ylcarboxamido) benzamidoacetic acid, m.p. 117°, from benzyl 3-(4-CBZ-amidinopiperazin-1-ylcarboxamido) benzamidoacetate (FAB 573; obtainable by condensing 3-(4-CBZ-amidinopiperazin-1-ylcarboxamido)benzoic acid with benzyl glycinate);

N-(3-(2-oxopiperazin-1-ylacetamido)benzoyl)-L-aspartic acid, FAB 393, from dibenzyl N-(3-(4-CBZ-2-oxopiperazin-1-ylacetamido)benzoyl)-L-aspartate (FAB 707; obtainable by condensing 3-(4-CBZ-2-oxopiperazin-1-ylacetamido)benzoic acid with dibenzyl L-aspartate);

N-(3-(4-amidino-2-oxopiperazin-1-ylacetamido)benzoyl) L-aspartic acid, m.p. 179°, from dibenzyl N-(3-(4-CBZ-amidino-2-oxopiperazin-1-ylacetamido) benzoyl)-L-aspartate (FAB 749; obtainable by condensing 3-(4-CBZ-amidino-2-oxopiperazin-1-ylacetamido)benzoic acid with dibenzyl L-aspartate);

4-(3-(piperazin-1-ylcarboxamido)benzamido)butyric acid, FAB 335, from benzyl 4-(3-(4-CBZ-piperazin-1-ylcarboxamido)benzamido)butyrate (FAB 559; obtainable by condensing 3-(4-CBZ-piperazin-1-ylcarboxamido)benzoic acid with benzyl 4-aminobutyrate);

4-(3-(4-amidinopiperazin-1-ylcarboxamido)benzamido) butyric acid, m.p. 215°, from benzyl 4-(3-(4-CBZ-amidinopiperazin-1-ylcarboxamido)benzamido) butyrate (FAB 601; obtainable by condensing 3-(4-CBZ-amidinopiperazin-1-ylcarboxamido)benzoic acid with benzyl 4-aminobutyrate);

4-(3-(2-oxopiperazin-1-ylacetamido)benzamido)butyric acid, FAB 363, from benzyl 4-(3-(4-CBZ-2-oxopiperazin-1-ylacetamido)benzamido)butyrate (FAB 587; obtainable by condensing 3-(4-CBZ-2-oxopiperazin-1-ylacetamido)benzoic acid with benzyl 4-aminobutyrate);

4-(3-(4-amidino-2-oxopiperazin-1-ylacetamido) benzamido)butyric acid, m.p. 269°, from benzyl 4-(3-(4-CBZ-amidino-2-oxopiperazin-1-ylacetamido) benzamido)butyrate (FAB 629; obtainable by condensing 3-(4-CBZ-amidino-2-oxopiperazin-1-ylacetamido)benzoic acid with benzyl 4-aminobutyrate);

4-(3-(4-amidinopiperazin-1-ylacetamido)benzamido) butyric acid, m.p. 115°, from benzyl 4-(3-(4-CBZ-amidinopiperazin-1-ylacetamido)benzamido)butyrate (FAB 615; obtainable by condensing 3-(4-CBZ-amidinopiperazin-1-ylacetamido)benzoic acid with benzyl 4-aminobutyrate);

3-(3-(4-amidinopiperazin-1-yl)propionamido) benzamidoacetic acid, FAB 377, m.p. 268°, from benzyl 3-(3-(4-CBZ-amidino-piperazin-1-yl) propionamido)benzamidoacetate (FAB 601; obtainable by condensing 3-(3-(4-CBZ-amidinopiperazin-1-yl) propionamido)benzoic acid with benzyl glycinate);

3-(3-(3-(4-amidinopiperazin-1-yl)propionamido) benzamido)propionic acid, FAB 391, m.p. 200°, from benzyl 3-(3-(3-(4-CBZ-amidinopiperazin-1-yl) propionamido)benzamido)propionate (FAB 615; obtainable by condensing 3-(3-(4-CBZ-amidinopiperazin-1-yl)propionamido)benzoic acid with benzyl β-alaninate);

3-(4-(4-amidinopiperazin-1-ylcarboxamidoacetyl) piperazin-1-yl)propionic acid, FAB 370, m.p. 141°, from benzyl 3-(4-(4-CBZ-amidinopiperazin-1-ylcarboxamidoacetyl)piperazin-1-yl)propionate (FAB 594; obtainable by condensing 4-CBZ-amidinopiperazin-1-ylcarboxamidoacetic acid with benzyl 3-(piperazin-1-yl)propionate);

3-(4-(4-amidinopiperazin-1-ylacetyl)piperazin-1-yl) propionic acid, m.p. 280°, from benzyl 3-(4-(4-CBZ-amidinopiperazin-1-ylacetyl)piperazin-1-yl)propionate (FAB 551; obtainable by condensing 4-CBZ-amidinopiperazin-1-ylacetic acid with benzyl 3-(piperazin-1-yl)propionate);

methyl 3-(3-(4-amidinopiperazin-1-ylacetamido) benzamido)propionate, dihydrochloride m.p. 222°, from methyl 3-(3(4-CBZ-amidinopiperazin-1-ylacetamido) benzamido)propionate (FAB 525; obtainable by condensing 4-CBZ-amidinopiperazin-1-ylacetic acid with methyl 3-(3-aminobenzamido) propionate);

3-(4-(4-guanidinobenzoyl)piperazin-1-yl)propionic acid, FAB 320, from benzyl 3-(4-(4-(3-CBZ-guanidino) benzoyl)piperazin-1-yl)propionate (FAB 544; obtainable by condensing 4-(3-CBZ-guanidino)benzoic acid with benzyl 3-(piperazin-1-yl)propionate);

4-(4-guanidinobenzamidoacetyl)piperazin-1-ylacetic acid, FAB 363, from benzyl 4-(4-(3-CBZ-guanidino) benzamidoacetyl)piperazin-1-ylacetate (FAB 587; obtainable by condensing 4-(3-CBZ-guanidino) benzamidoacetic acid with benzyl piperazin-1-ylacetate).

Example 3

(a) A mixture of 1.86 g of 4-aminopiperazin-1-ylacetic acid, 2.22 g of methyl 3-(3-aminobenzamido)propionate, 1.92 g of DAPECI hydrochloride, 1.01 g of N-methylmorpholine and 70 ml of DMF is stirred for 16 hours at 20°. It is evaporated and the residue is worked up with ethyl acetate/5% NaHCO₃ solution to give methyl 3-(3-(4-amidinopiperazin-1-ylacetamido)benzamido) propionate. Dihydrochloride m.p. 222°.

The following are obtained analogously by condensation:

methyl 4-(4-(4-guanidinobenzoyl)piperazin-1-yl)butyrate from 4-guanidinobenzoic acid with methyl 4-(piperazin-1-yl)butyrate;

methyl 4-(4-guanidinobenzamidoacetyl)piperazin-1-ylacetate from 4-guanidinobenzoic acid with methyl 4-aminoacetylpiperazin-1-ylacetate;

methyl 3-(piperazin-1-ylcarboxamidoacetamido) benzamidoacetate from 3-(piperazin-1-ylcarboxamidoacetamido)benzoic acid with methyl glycinate;

methyl 3-(3-(4-amidinopiperazin-1-ylcarboxamidoacetamido)benzamido)propionate from 3-(4-amidinopiperazin-1-ylcarboxamidoacetamido) benzoic acid and methyl β-alaninate;

methyl 4-(4-amidinopiperazin-1-ylacetyl)piperazin-1-ylacetate from 4-amidinopiperazin-1-ylacetic acid with methyl piperazin-1-ylacetate;

methyl 3-(3-(2-oxopiperazin-1-ylacetamido)benzamido) propionate from 3-(2-oxopiperazin-1-ylacetamido) benzoic acid with methyl β-alaninate;

methyl 3-(4-amidino-2-oxopiperazin-1-ylacetamido) benzamidoacetate from 3-(4-amidino-2-oxopiperazin-1-ylacetamido)benzoic acid with methyl glycinate;

methyl 3-(3-(4-amidino-2-oxopiperazin-1-ylacetamido) benzamido)propionate from 3-(4-amidino-2-oxopiperazin-1-ylacetamido)benzoic acid with methyl β-alaninate;

methyl 4-(4-amidinopiperazin-1-ylcarboxamidoacetyl) piperazin-1-ylacetate from 4-amidinopiperazin-1-ylcarbox amidoacetic acid with methyl piperazin-1-ylacetate;

methyl 4-(4-guanidinobenzoyl)-2-oxopiperazin-1-ylacetate from 4-guanidinobenzoic acid with methyl 2-oxopiperazin-1-ylacetate;

methyl 3-(4-amidinopiperazin-1-ylcarboxamidoacetamido)benzamidoacetate from 3-(4- amidinopiperazin-1-ylcarboxamidoacetamido)benzoic acid with methyl glycinate;

methyl 3-(4-amidinopiperazin-1-ylacetamido) benzamidoacetate from 3-(4-amidinopiperazin-1-ylacetamido)benzoic acid with methyl glycinate;

methyl 4-(4-(4-amidinopiperazin-1-ylacetyl)piperazin-1-yl)butyrate from 4-amidinopiperazin-1-ylacetic acid with methyl 4-(piperazin-1-yl)butyrate;

methyl 3-(4-(4-guanidinobenzoyl)-2-oxopiperazin-1-yl)propionate from 4-guanidinobenzoic acid with methyl 3-(2-oxopiperazin-1-yl)propionate;

methyl 3-(3-(4-amidinopiperazin-1-ylcarboxamido)benzamido)propionate from 3-(4-amidinopiperazin-1-ylcarboxamido)benzoic acid with methyl β-alaninate;

methyl 3-(4-amidinopiperazin-1-ylcarboxamido) benzamidoacetate from 3-(4-amidinopiperazin-1-ylcarboxamido)benzoic acid with methyl glycinate;

dimethyl N-(3-(4-amidino-2-oxopiperazin-1-ylacetamido)benzoyl)-L-aspartate from 3-(4-amidino-2-oxopiperazin-1-ylacetamido)benzoic acid with dimethyl L-aspartate;

methyl 4-(3-(4-amidinopiperazin-1-ylcarboxamido)benzamido)butyrate from 3-(4-amidinopiperazin-1-ylcarboxamido)benzoic acid with methyl 4-aminobutyrate;

methyl 4-(3-(4-amidino-2-oxopiperazin-1-ylacetamido)benzamido)butyrate from 3-(4-amidino-2-oxopiperazin-1-ylacetamido)benzoic acid with methyl 4-aminobutyrate;

methyl 3-(3-(4-amidinopiperazin-1-yl)propionamido)benzamidoacetate from 3-(3-(4-amidinopiperazin-1-yl)propionamido)benzoic acid with methyl glycinate;

methyl 3-(3-(3-(4-amidinopiperazin-1-yl)propionamido)benzamido)propionate from 3-(3-(4-amidinopiperazin-1-yl)propionamido)benzoic acid with methyl β-alaninate;

methyl 3-(4-(4-amidinopiperazin-1-ylcarboxamidoacetyl)piperazin-1-yl)propionate from 4-amidinopiperazin-1-ylcarboxamidoacetic acid with methyl 3-(piperazin-1-yl)propionate;

methyl 3-(4-(4-amidinopiperazin-1-ylacetyl)piperazin-1-yl)propionate from 4-amidinopiperazin-1-ylacetic acid with methyl 3-(piperazin-1-yl)propionate;

ethyl 3-(3-(4-amidinopiperazin-1-ylacetamido)benzamido)propionate from 3-(4-amidinopiperazin-1-ylacetyl)benzoic acid with ethyl β-alaninate.

Example 4

(a) A solution of Li—N(Si(CH$_3$)$_3$)$_2$ in 20 ml of THF, freshly prepared from C$_4$H$_9$Li and 1.13 g of hexamethyldisilazane, is added dropwise at −78°, with stirring, to a solution of 3.15 g of ethyl 3-(4-(4-cyanobenzoyl)piperazin-1-yl)propionate (FAB 316; obtainable by reacting 4-cyanobenzoyl chloride with ethyl piperazin-1-ylpropionate) in 50 ml of THF. The mixture is left to warm up to 20°, with stirring, aqueous hydrochloric acid is added, the mixture is washed with ethyl acetate, sodium hydroxide solution is added to pH 7.5 and the mixture is worked up in conventional manner and evaporated to give ethyl 3-(4-(4-amidinobenzoyl)piperazin-1-yl)propionate, FAB 333.

Ethyl 4-(4-(4-amidinobenzoyl)piperazin-1-yl)butyrate, FAB 347, is obtained analogously from ethyl 4-(4-(4-cyanobenzoyl)piperazin-1-yl)butyrate (FAB 330).

(b) By saponification analogously to Example 1, 3-(4-(4-amidinobenzoyl)piperazin-1-yl)propionic acid, FAB 305, and 4-(4-(4-amidinobenzoyl)piperazin-1-yl)butyric acid, FAB 319, are obtained from the ethyl esters mentioned above under (a).

Example 5

0.17 ml of ethyldiisopropylamine is added to a solution of 201 mg of 1-amidino-3,5-dimethylpyrazole nitrate in 17 ml of dioxane and 5 ml of water and the mixture is stirred for 15 minutes. 357 mg of 3-(3-(piperazin-1-ylcarboxamido)benzamido)propionic acid hydrochloride (FAB 321; obtainable by reacting benzyl 3-(3-aminobenzamido)propionate with diphosgene to give benzyl 3-(3-isocyanatobenzamido)propionate, adding on 1-BOC-piperazine to give benzyl 3-(3-(4-BOC-piperazin-1-ylcarboxamido)benzamido)propionate, cleaving the BOC group with 4 N HCl in dioxane to give benzyl 3-(3-(piperazin-1-ylcarboxamido)benzamido)propionate hydrochloride (FAB 411) and hydrogenolyzing on 5% Pd/C) and a further 0.17 ml of ethyldiisopropylamine are then added, the mixture is boiled for 45 hours and evaporated, the residue is dissolved in water and the solution is washed with ether and then with ethyl acetate and evaporated again to give 3-(3-(4-amidinopiperazin-1-ylcarboxamido)benzamido)propionic acid, m.p. 234° (decomposition).

The 4-amidinopiperazine derivatives indicated in Example 2 are obtained analogously from the corresponding piperazine derivatives.

Example 6

Analogously to Example 5, there is obtained with 1-amidino-3,5-dimethylpyrazole-nitrate:

from 3-(4-(1-piperazinyl-carboxamido-acetyl)-1-piperazinyl)-propionic acid:
3-(4-(4-amidino-1-piperazinyl-carboxamido-acetyl)-1-piperazinyl)propionic acid, m.p. 141°;

from 3-(3-(1-piperazinyl)-propionamido)-benzamido-acetic acid:
3-(3-(4-amidino-1-piperazinyl)-propionamido)-benzamido-acetic acid, m.p. 268°;

from 3-(3-(3-(1-piperazinyl)-propionamido)-benzamido)-propionic acid:
3-(3-(3-(4-amidino-1-piperazinyl)-propionamido)-benzamido)-propionic acid, m.p. 200°;

from 3-(3-(2-(1-piperazinyl)-propionamido)-benzamido)-propionic acid:
3-(3-(2-(4-amidino-1-piperazinyl)-propionamido)-benzamido)-propionic acid, m.p. 171°;

from 3-(3-(1-piperazinyl-acetamido)-benzamido)-propionic acid:
3-(3-(4-amidino-1-piperazinyl-acetamido)-benzamido)-propionic acid, dihydrochloride, m.p. 272°.

The Examples which follow relate to pharmaceutical preparations.

Example A

Tablets

A mixture of 1 kg of an active ingredient of formula I, 4 kg of lactose, 1.2 kg of maize starch, 200 g of talc and 100 g of magnesium stearate is compressed to tablets in conventional manner so that each tablet contains 100 mg of active ingredient.

Example B

Coated Tablets

Tablets are formed by compression analogously to Example A and then provided in conventional manner with a coating of sucrose, maize starch, talc, tragacanth and color.

Example C

Capsules 500 g of an active ingredient of formula I are filled into hard gelatin capsules in conventional manner so that each capsule contains 500 mg of active ingredient.

Example D

Injection Vials

A solution of 100 g of an active ingredient of formula I in 4 l of double-distilled water is adjusted to pH 6.5 with 2 N hydrochloric acid, filtered under sterile conditions and filled into injection vials. After lyophilization under sterile conditions, the vials are sealed under sterile conditions. Each injection vial contains 50 mg of active ingredient.

Example E

Suppositories

A mixture of 50 g of an active ingredient of formula I with 10 g of soya lecithin and 140 g of cacao butter is melted, poured into molds and left to cool. Each suppository contains 250 mg of active ingredient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula I:

$$Y-(C_mH_{2m}-CHR^1)_n-CO-(NH-CHR^2-CO)_r-Z \quad I$$

wherein

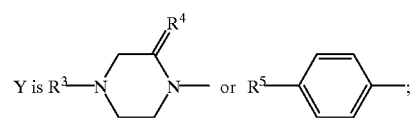

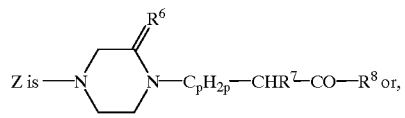

if Y is $R^3$— 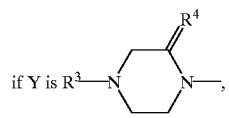

Z can also be

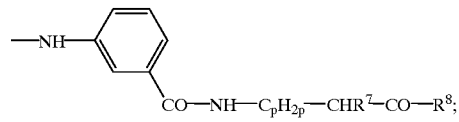

$R^1$, $R^2$ and $R^7$ are each, independently, $-C_tH_{2t}-R^9$, benzyl or hydroxybenzyl;

$R^3$ is H or $H_2N-C(=NH)-$;

$R^4$ is (H,H) or $=O$;

$R^6$ is (H,H);

$R^5$ is $H_2N-C(=NH)-NH-$;

$R^8$ is OH, OA or NHOH;

$R^9$ is H or COOH;

A is in each case, independently, alkyl having 1–4 C atoms;

m and t are each, independently, 0, 1, 2, 3 or 4;

n and r are each, independently, 0 or 1; and p is 0, 1 or 2;

wherein piperazine rings are unsubstituted or substituted by 1 to 4 groups A; or a salt thereof.

2. A compound according to claim 1, wherein said compound is:

3-(3-(4-amidinopiperazin-1-ylacetamido)benzamido)-propionic acid or a salt thereof.

3. A compound according to claim 1, wherein $R^1$, $R^2$ and $R^7$ are each H.

4. A compound according to claim 1, wherein $R^3$ is $H_2N-C(=NH)-$.

5. A compound according to claim 1, wherein $R^4$ is (H,H).

6. A compound according to claim 1, wherein $R^8$ is OH, $OCH_3$ or $OC_2H_5$.

7. A compound according to claim 1, wherein the group $-(C_mH_{2m}-CHR^1)_n-CO-(NH-CHR^2CO)_r-$ is $-CO-$, $-CH_2-CO-$, $-CO-NH-CH_2-CO-$ or $-CH_2CH_2-CO-$.

8. A compound according to claim 1, wherein the piperazine rings in said compound are unsubstituted or substituted by 1–4 methyl groups.

9. A compound according to claim 1, wherein Y is

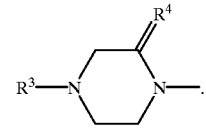

10. A compound according to claim 1, wherein Y is

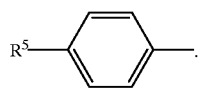

11. A compound according to claim 1, wherein Y is

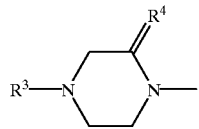

and Z is

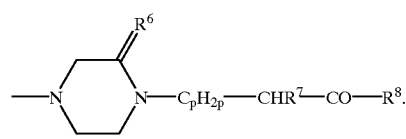

12. A compound according to claim 1, wherein Y is

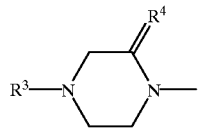

and Z is

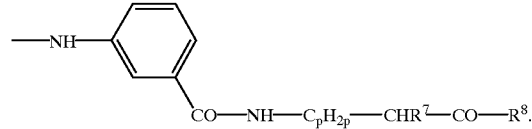

13. A compound according to claim 1, wherein Y is

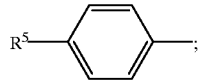

and Z is

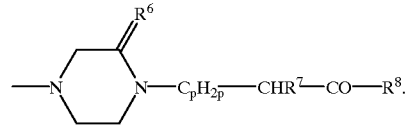

14. A compound according to claim 1, wherein Y is

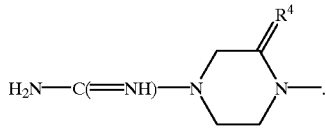

15. A compound according to claim 1, wherein Y is

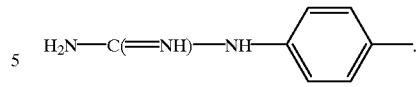

16. A compound according to claim 1, wherein the group $-C_pH_{2p}-CHR^7-CO-R^8$ is $-CH_2COOH$, $-CH_2CH_2COOH$, $-(CH_2)_3-COOH$, $-CH(COOH)-CH_2COOH$, $-CH_2COOA$, $-CH_2CH_2COOA$, or $-(CH_2)_3-COOA$.

17. A compound according to claim 11, wherein the group $-C_pH_{2p}-CHR^7-CO-R^8$ is $-CH_2COOH$, $-CH_2CH_2COOH$, $-(CH_2)_3COOH$, $-CH(COOH)-CH_2COOH$, $-CH_2COOA$, $-CH_2CH_2COOA$ or $-(CH_2)_3COOA$.

18. A compound according to claim 12, wherein the group $-C_pH_{2p}-CHR^7-CO-R^8$ is $-CH_2COOH$, $-CH_2CH_2COOH$, $-(CH_2)_3COOH$, $-CH(COOH)-CH_2COOH$, $-CH_2COOA$, $-CH_2CH_2COOA$ or $-(CH_2)_3COOA$.

19. A compound according to claim 15, wherein the group $-C_pH_{2p}-CHR^7-CO-R^8$ is $-CH_2COOH$, $-CH_2CH_2COOH$, $-(CH_2)_3COOH$, $-CH(COOH)-CH_2COOH$, $-CH_2COOA$, $-CH_2CH_2COOA$ or $-(CH_2)_3COOA$.

20. A compound of formula I:

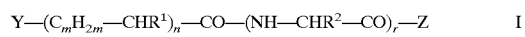

wherein

Y is 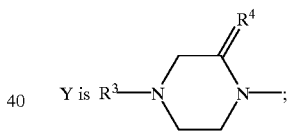

Z is 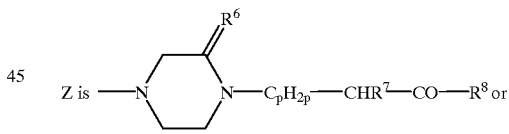 or

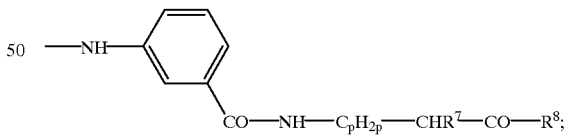

$R^1$, $R^2$ and $R^7$ are each, independently, $-C_tH_{2t}-R^9$, benzyl or hydroxybenzyl;

$R^3$ is H or $H_2N-C(=NH)-$;

$R^4$ and $R^6$ are each, independently, (H,H) or =O;

$R^8$ is OH, OA or NHOH;

$R^9$ is H or COOH;

A is in each case, independently, alkyl having 1–4 C atoms;

m and t are each, independently, 0, 1, 2, 3 or 4;

n and r are each, independently, 0 or 1; and p is 0, 1 or 2;

wherein piperazine rings are unsubstituted or substituted by 1 to 4 groups A; or salts thereof.

21. A pharmaceutical composition comprising an effective amount of a compound according to formula I of claim 1 or a physiologically acceptable salt thereof, and a physiologically acceptable carrier.

22. A composition according to claim 19, wherein said composition contains 5 mg–1 g of said compound.

23. A composition according to claim 21, wherein said compound is:

3-(3-(4-amidinopiperazin-1-ylacetamido)benzamido) propionic acid or a salt thereof.

24. A composition according to claim 21, wherein said compound is:

methyl 3-(3-(4-amidinopiperazin-1-ylacetamido) benzamido)propionate.

25. A method for the treatment of thrombosis, comprising administering to a patient an effective amount of a compound according to formula I of claim 1 or a physiologically acceptable salt thereof.

26. A method according to claim 25, wherein said compound is administered in a daily dosage of 0.1–20 mg/kg of body weight.

27. A compound according to claim 1, wherein said compound is:

methyl 3-(3-(4-amidinopiperazin-1-ylacetamido) benzamido)propionate.

* * * * *